US007365323B2

(12) United States Patent
Ohtaki et al.

(10) Patent No.: US 7,365,323 B2
(45) Date of Patent: Apr. 29, 2008

(54) ENVIRONMENTAL SCANNING ELECTRON MICROCOPE

(75) Inventors: Tomohisa Ohtaki, Hitachinaka (JP); Kenichi Hirane, Hitachi (JP); Ryoichi Ishii, Hitachinaka (JP); Haruhisa Takahata, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 260 days.

(21) Appl. No.: 11/354,067

(22) Filed: Feb. 15, 2006

(65) Prior Publication Data

US 2006/0219912 A1 Oct. 5, 2006

(30) Foreign Application Priority Data

Mar. 16, 2005 (JP) ............................ 2005-074774

(51) Int. Cl.
*H01J 37/28* (2006.01)

(52) U.S. Cl. ...................... 250/310; 250/309; 250/311

(58) Field of Classification Search ................ 250/310, 250/311, 396 R, 309, 397
See application file for complete search history.

(56) References Cited

U.S. PATENT DOCUMENTS 5,008,537 A * 4/1991 Toita et al. ................ 250/309
5,362,964 A 11/1994 Knowles et al.
5,412,211 A 5/1995 Knowles
6,583,413 B1 * 6/2003 Shinada et al. ............ 250/310
7,098,455 B2 * 8/2006 Shinada et al. ............ 250/310
2005/0029467 A1 * 2/2005 Yu et al. ............... 250/442.11
2007/0215803 A1 * 9/2007 Iwabuchi et al. .......... 250/310

FOREIGN PATENT DOCUMENTS

JP 01-183047 7/1989
JP 2000-156192 6/2000

* cited by examiner

*Primary Examiner*—Jack I. Berman
*Assistant Examiner*—Johnnie L Smith, II
(74) *Attorney, Agent, or Firm*—McDermott Will & Emery LLP

(57) ABSTRACT

In an environmental scanning electron microscope in which differential pumping for maintaining the pressure ratio between an electron optical system and a specimen chamber at a predetermined value is effected and a probe electric current is conditioned to meet a predetermined or more value so as to permit observation of uncooked food and moist specimens in low vacuum, there are provided three stages of objective apertures used as apertures for an objective lens for an electron beam in the electron optical system and used also as orifices for differential pumping for maintaining the pressure ratio between the electron optical system and the specimen chamber at a predetermined value. Then, a deflection fulcrum of the electron beam in the electron optical system is set at a mid stage of the three-stage objective aperture.

7 Claims, 6 Drawing Sheets

ENVIRONMENTAL SCANNING ELECTRON MICROCOPE

BACKGROUND OF THE INVENTION

The present invention relates to improvements on the electron optical system of an environmental scanning electron microscope suitable for observation of uncooked food or moist specimens.

In a scanning electron microscope (SEM) being suitable for observation of specimens in natural condition such as uncooked food or moist specimens and called an environmental or low-vacuum SEM, an electron gun chamber is maintained at high vacuum, whereas a specimen chamber is maintained at low vacuum approximating natural condition. Specifically, the electron gun chamber included in an electron optical system is at $10^{-2}$ Pa to $10^{-4}$ Pa but the specimen chamber is at several Pa to several of hundreds of Pa.

U.S. Pat. Nos. 5,362,964 and 5,412,211 disclose an environmental SEM having two orifices and a cylindrical electron beam path in order to be constructed such that differential pumping is effected through substantially three steps of evacuation conductance to assure a large pressure ratio between the electron optical system and the specimen chamber.

And also, JP-A-1-183047 discloses an SEM capable of observing specimens in natural condition, which is constructed to have three stages of orifices for differential pumping.

In the construction disclosed in the aforementioned US Patents, however, the deflection area on the surface of a specimen is restricted by the disposition of the cylindrically extensional pressure orifice. Further, the distance from an excitation point of objective lens to the specimen surface is long and disadvantageously, the resolution the SEM can exhibit is degraded.

In the case of JP-A-1-183047, the deflection area on the specimen surface is likewise liable to be restricted as gathering from the illustrated construction and besides, the specimen surface is situated remotely from an excitation point of objective lens and the resolution the SEM exhibits is considered to be hardly improved.

SUMMARY OF THE INVENTION

An object of the present invention is to assure a sufficiently wide deflection area on a specimen holder in an environmental scanning microscope in which differential pumping for maintaining a predetermined value of pressure ratio between the electron optical system and the specimen chamber needs to be effected and a predetermined or more amount of probe electric current is necessary to obtain images of high quality.

Another object of the invention is to provide an environmental SEM of high resolution performance.

According to one aspect of the invention, in an environmental scanning microscope comprising three stages of objective apertures used as apertures for an objective lens functioning to focus an electron beam emitted from an electron source and used also as orifices for differential pumping between an electron optical system and a specimen chamber, a fulcrum of deflection of the electron beam in the electron optical system is set substantially at a mid stage of the three-stage objective aperture.

According to another aspect of the invention, a lens principal plane of the objective lens is also set substantially at the mid stage of the three-stage objective aperture.

In a preferred embodiment of the invention, an environmental scanning electron microscope can be provided which can assure a sufficiently wide deflection area on a specimen holder.

Further, in the preferred embodiment of the invention, an environmental scanning electron microscope having high resolution performance can be provided.

Other objects and features of the present invention will become apparent in embodiments described hereinafter in conjunction with the accompanying drawings.

DETAILED DESCRIPTION OF THE INVENTION

Figure 1:
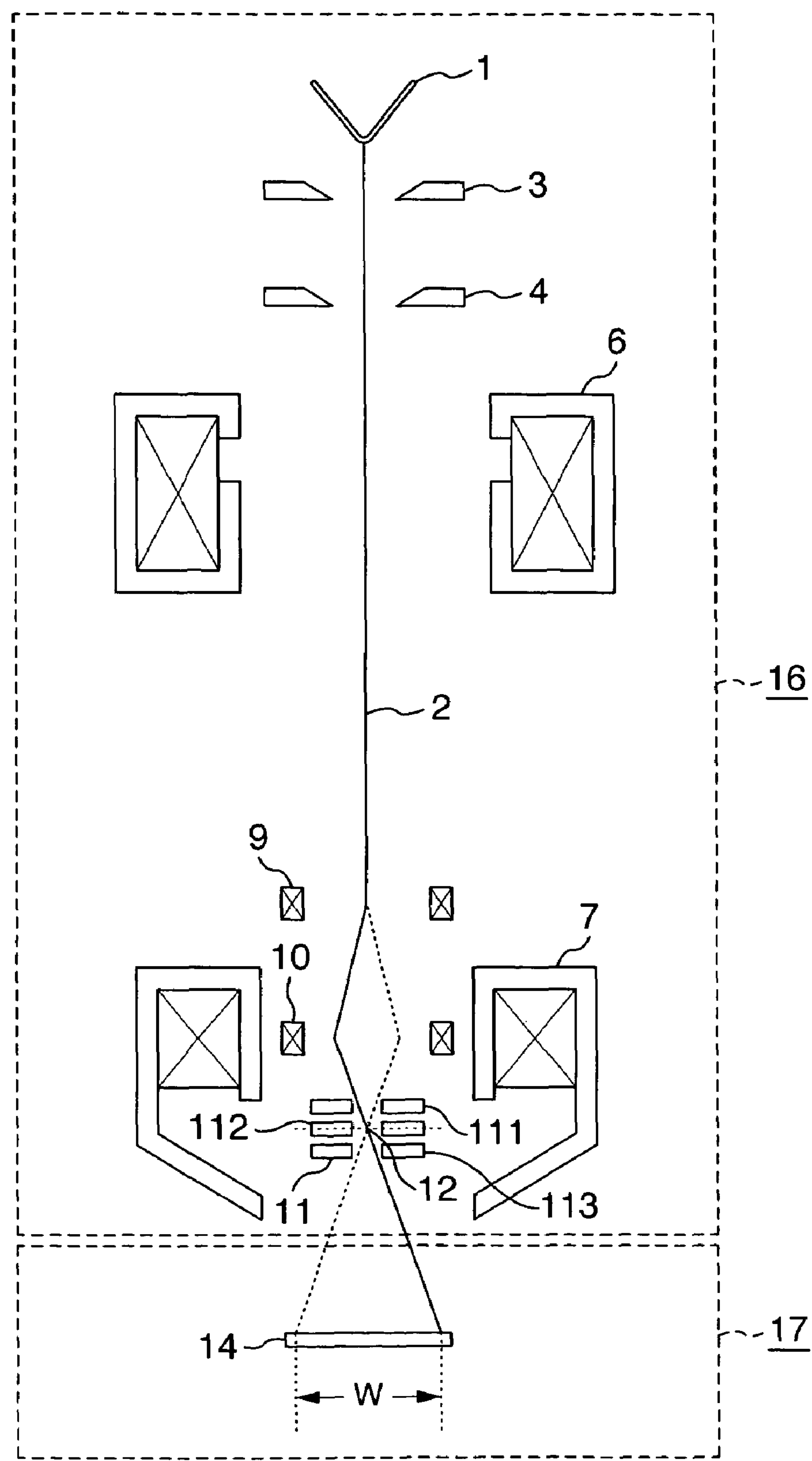
FIG. 1 is a diagram schematically showing a deflection area defined by an electron optical system of an environmental scanning electron microscope according to an embodiment of the present invention.
Figure 2:
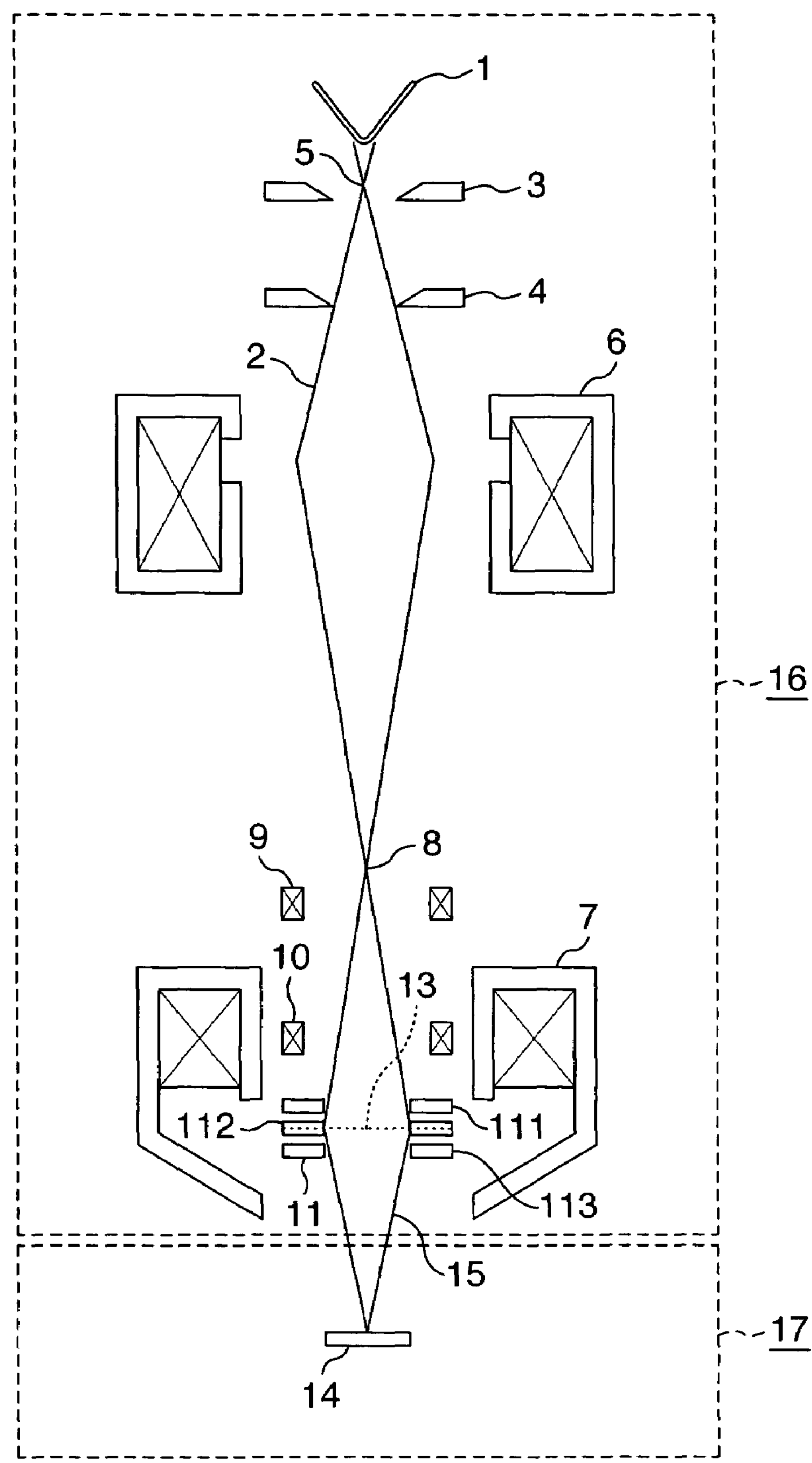
FIG. 2 is a diagram schematically showing the state of an electron beam deflected and irradiated on the surface of a specimen by the electron optical system of the environmental scanning electron microscope in the embodiment.

Referring now to FIG. 1, an example of construction of an electron optical system of an environmental scanning electron microscope (SEM) and a deflection area according to an embodiment of the present invention are illustrated schematically. Schematically illustrated in FIG. 2 is the state of an electron beam irradiated on the surface of a specimen by the electron optical system of the environmental SEM in the embodiment.

An electron beam 2 emitted from an electron source 1 is subjected to the convergence action and is curved in its trajectory under the influence of potential at a Whenelt electrode 3 so as to be formed into a first cross over 5 (FIG. 2) between the Whenelt electrode 3 and an accelerating electrode 4. Further, the electron beam 2 accelerated by an accelerating voltage is passed through the accelerating electrode 4 and converged by a condenser lens 6 so as to be formed into a second cross over 8 (FIG. 2) between the condenser lens 6 and an objective lens 7. Subsequently, the electron beam 2 is curved in its trajectory by means of an upper deflector 9, again curved in its trajectory by means of a lower deflector 10 and then restricted in its passage area by means of an objective aperture (assembly) 11. In the objective aperture 11, the electron beam 2 passes through a deflection fulcrum 12 shown in FIG. 1 and an objective lens principal plane 13 shown in FIG. 2, thus being ultimately irradiated on the surface of a specimen holder 14. A current ultimately irradiated on the surface of a specimen is called a probe electric current 15. In the low-vacuum SEM mode, the objective aperture 11 also plays the role of an orifice (assembly) for materializing differential pumping between an electron optical system 16 ($10^{-2}$ Pa to $10^{-4}$ Pa) and a specimen chamber 17 (several Pa to several of hundreds of Pa).

In the present embodiment, the objective aperture 11 has three stages of upper aperture 111, mid aperture 112 and lower aperture 113 and as shown in FIG. 1, the fulcrum of deflection 12 of the electron beam caused by the upper and lower deflectors 9 and 10 is so set as to be positioned at the mid aperture 112. In addition, as shown in FIG. 2, the lens principal plane 13 of objective lens 7 is so set as to be positioned also at the mid aperture 112 of three-stage aperture 11.

In the present embodiment, the evacuation conductance is maintained by the three objective apertures (used also as orifices) 111, 112 and 113 and the deflection fulcrum 12 of the electron beam 2 deflected by means of the upper and lower deflectors 9 and 10 is set around the mid aperture 112 which is substantially a middle part of the three-stage objective aperture 11. Therefore, within the range of a hole diameter of three-stage objective aperture 11 restricted for the purpose of maintaining the vacuum pressure ratio between electron optical system 16 and specimen chamber 17 at a predetermined value, a wide deflection area can be assured on the surface of specimen holder 14.

Then, as shown in FIG. 2, the electron beam 2 having passed through the objective aperture 11 is subjected to focusing at the lens principal plane 13 of objective lens 7 so as to be deflected toward the surface of specimen holder 14. For convenience of explanation, the hole diameter of three-stage objective aperture 11 is illustrated in a more enlarged form in FIG. 2 than in FIG. 1. As will be seen from FIG. 2, the lens principal plane 13 of objective lens 7 is set around the mid aperture 112 which is substantially a middle part of three-stage objective aperture 11. With this construction, the electron beam can be deflected/irradiated without distortion even when the excitation strength of objective lens is changed.

Figure 3:
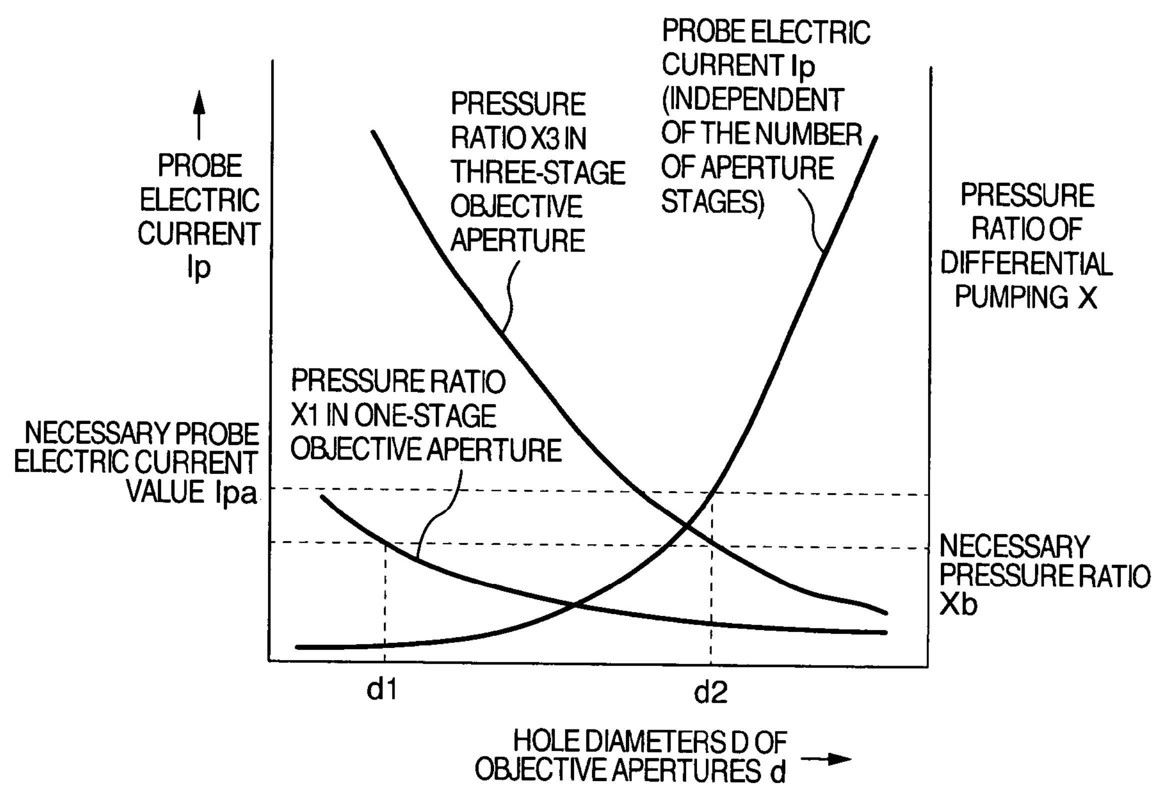
FIG. 3 is a graph showing probe electric current values and pressure ratios of differential pumping in relation to hole diameters of objective apertures.

Turning now to FIG. 3, there is illustrated a graph depicting value Ip of probe electric current 15 and pressure ratio X in relation to the hole diameter of objective aperture 11. When required values of the probe electric current Ip and pressure ratio X are Ipa and Xb, respectively, as shown at dotted line in the figure, one stage of objective aperture cannot satisfy both the values simultaneously. For example, at the aperture hole diameter being d1, the required pressure ratio Xb of differential pumping can be satisfied on a characteristic curve of pressure ratio X1 obtained with one objective aperture but the required probe electric current value Ipa cannot at all be satisfied on a characteristic curve of probe electric current Ip. Further, at the aperture hole diameter being d2, the probe electric current value Ipa is satisfied but the required pressure ratio Xb cannot be satisfied.

On the contrary, with the structure of three-stage objective aperture 11 (111, 112 and 113), it is demonstrated that at the aperture hole diameter being d2, the probe electric current value Ipa and pressure ratio Xb can be satisfied simultaneously as shown at a characteristic curve of pressure ratio X3.

Figure 4:
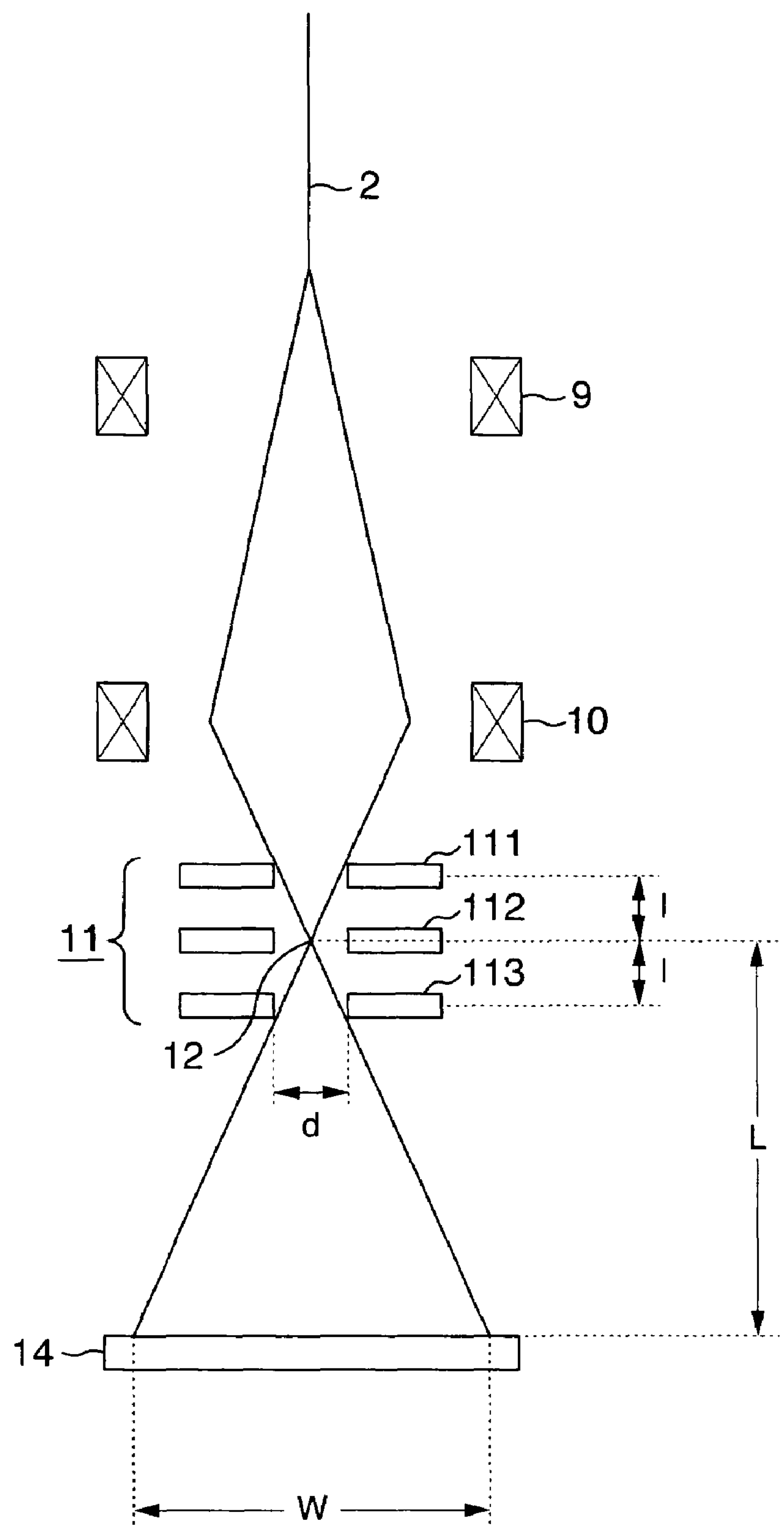
FIG. 4 is an enlarged diagram of the essential part in FIG. 1.

The aforementioned feature of the present embodiment will now be expressed mathematically using geometrical dimensions indicated in FIG. 4 exaggeratedly showing geometrical dimensions of the essential part in FIG. 1.

When the structure of three-stage objective aperture 11 is adopted under the condition that each of the three apertures (also serving as orifices) 111, 112 and 113 has the same hole diameter, relational expressions (1) to (3) stand. By using these expressions, propriety of the balance between the probe electric current Ip and the pressure ratio X in differential pumping can be obtained.

$$4L^2Ip/\pi^2D^2\beta<d^2<3S/29\pi(X-1) \quad (1)$$

$$4L^2Ip/\pi^2D^2\beta=d_a^2 \quad (2)$$

$$3S/29\pi(X-1)=d_b^2 \quad (3)$$

where Ip represents probe electric current value (A), D represents probe diameter (m), β represents brightness ($A/m^2\cdot str$), S represents effective pumping speed ($m^3/s$) for evacuating the electron optical system, X represents pressure ratio of differential pumping, L represents distance (m) from the surface irradiated with the electron beam to the objective aperture and d represents hole diameter (m) of aperture.

Aperture hole diameter $d_a$ is determined by factors inclusive of the required probe electric current Ip on the side of the electron optical system 16, whereas the aperture hole diameter $d_b$ is determined by factors inclusive of the required pressure ratio X for differential pumping on the side of the vacuum evacuation system 17. The above expressions are obtained by modifying theoretical expressions concerning the probe electric current Ip in the electron optical system 16 and the vacuum evacuation, respectively. In designing, a value of the magnitude of probe electric current Ip necessary for obtaining an image of high quality and a required value of pressure ratio X for differential pumping are substituted into the above expressions to thereby determine a hole diameter of the three-stage objective aperture 11. Further, since $d_a<d_b$ must stand, the pumping speed of a pump and evacuation conductance need to be taken into consideration in the phase of design.

In the US Patents described previously, the two orifices and cylindrical electron beam path are provided and therefore, it appears that a differential pumping system based on three steps of evacuation conductance can substantially be established. But, the extensional pressure orifice disposed at the lowermost stage restricts the deflection area on the specimen holder. In contrast therewith, according to the present embodiment of the invention, (1) the deflection fulcrum 12 of electron beam 2 deflected by the upper and lower deflectors 9 and 10 is set at the mid stage 112 of three-stage objective aperture 11 so that a wide deflection area may be assured on the specimen holder surface as shown in FIG. 1 and (2) the lens principal plane 13 of objective lens 7 is set at the mid stage 112 of three-stage objective aperture (also playing the role of orifices assembly) 11 so that the electron beam may be deflected/irradiated without distortion even when the excitation strength of objective lens is changed.

Subsequently, in the present embodiment, a deflection area W on the specimen holder 14 can be determined pursuant to expression (4) by using geometrical dimensions shown in FIG. 4.

$$W=L\times d/l \quad (4)$$

where W represents the deflection area on the specimen, L represents the distance from the surface of specimen holder to deflection fulcrum 12, l (small letter of L) represents the distance between adjacent ones of upper, mid and lower apertures 111, 112 and 113 of three-stage objective aperture 11 and d represents the aperture hole diameter.

Accordingly, in the presence of the long distance to the extensional pressure orifice at the lowermost stage as in the case of the previously-described US Patents, the inter-aperture stage distance l in the three-stage objective aperture 11 increases and obviously, the deflection area W on specimen holder 14 is narrowed. On the contrary, according to the present embodiment, by setting the fulcrum of deflection 12 by the upper and lower deflectors 9 and 10 at the position of the mid aperture 112 representing the substantially middle part of three-stage aperture 11, a sufficiently wide deflection area W can be assured on the specimen holder 14 with the limited aperture hole diameter d.

When a necessary deflection area W is determined using the aforementioned expressions, the aperture hole diameter d and inter-aperture stage distance l required at the least can be determined. In choosing an aperture hole diameter d from the aforementioned expressions, a condition indicated by expression (5) needs to be taken into account and an aperture hole diameter d simultaneously satisfying the conditions of the previously-described expressions (1) to (3) and the condition of expression (5) is chosen.

$$(W1/L)^2<3S/29\pi(X-1) \tag{5}$$

The foregoing embodiment of the present invention is directed to the environmental scanning electron microscope in which the objective aperture 11 adapted for the objective lens 7 functioning to focus the electron beam 2 emitted from the electron source 1 is combined with the orifice adapted for differential pumping between the electron optical system 16 and specimen chamber 17 to provide the structure of three-stage aperture (111 to 113). Then, the deflection fulcrum 12 of the electron beam 2 in the electron optical system 16 is set substantially at the mid stage 112 of three-stage objective aperture 11.

With the above construction, a wide deflection area can be assured on the specimen surface in the environmental SEM capable of increasing the pressure ratio of differential pumping and obtaining a necessary probe electric current to observe an image of high quality and in the SEM adopting the objective aperture of three-stage structure, a necessary amount of current can be assured to improve the resolution performance the SEM has.

Figure 5:
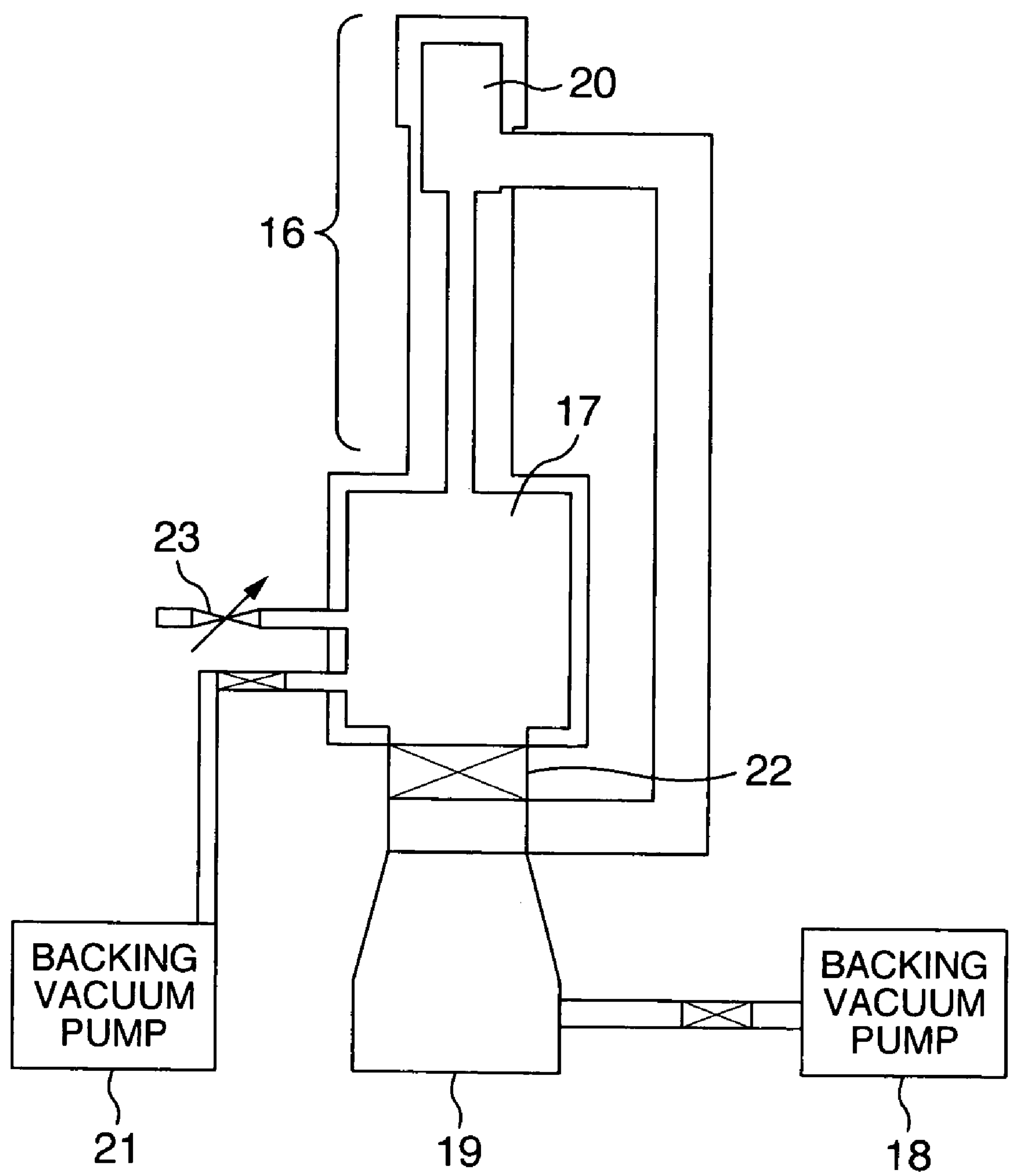
FIG. 5 is a diagram schematically showing an embodiment of a vacuum evacuation system of the environmental scanning electron microscope of the invention.

Referring now to FIG. 5, an embodiment of a vacuum evacuation system applicable to the environmental scanning electron microscope of the present invention is schematically constructed as shown therein. Concurrently with start of evacuation, pre-evacuation of main pump 19 and electron gun chamber 20 is effected by means of a backing vacuum pump 18 representing a first backing vacuum pump and evacuation of the specimen chamber 17 is effected by means of a backing vacuum pump 21 representing a second backing vacuum pump. After completion of the pre-evacuation, the interior of main pump 19 and the electron gun chamber 20 reach a vacuum pressure for permitting the main pump 19 to start and the main pump 19 is now started for the first time. Then, to evacuate the specimen chamber 17 to high vacuum pressure, a main valve 22 is opened. To set up the low-pressure SEM mode (specimen chamber vacuum pressure: several Pa to several of hundreds of Pa), the main valve 22 is closed, so that only the electron gun chamber 20 can be evacuated to high vacuum by means of the main pump 19 and the specimen chamber 17 can be controlled for low vacuum by means of a needle valve 23.

Figure 6:
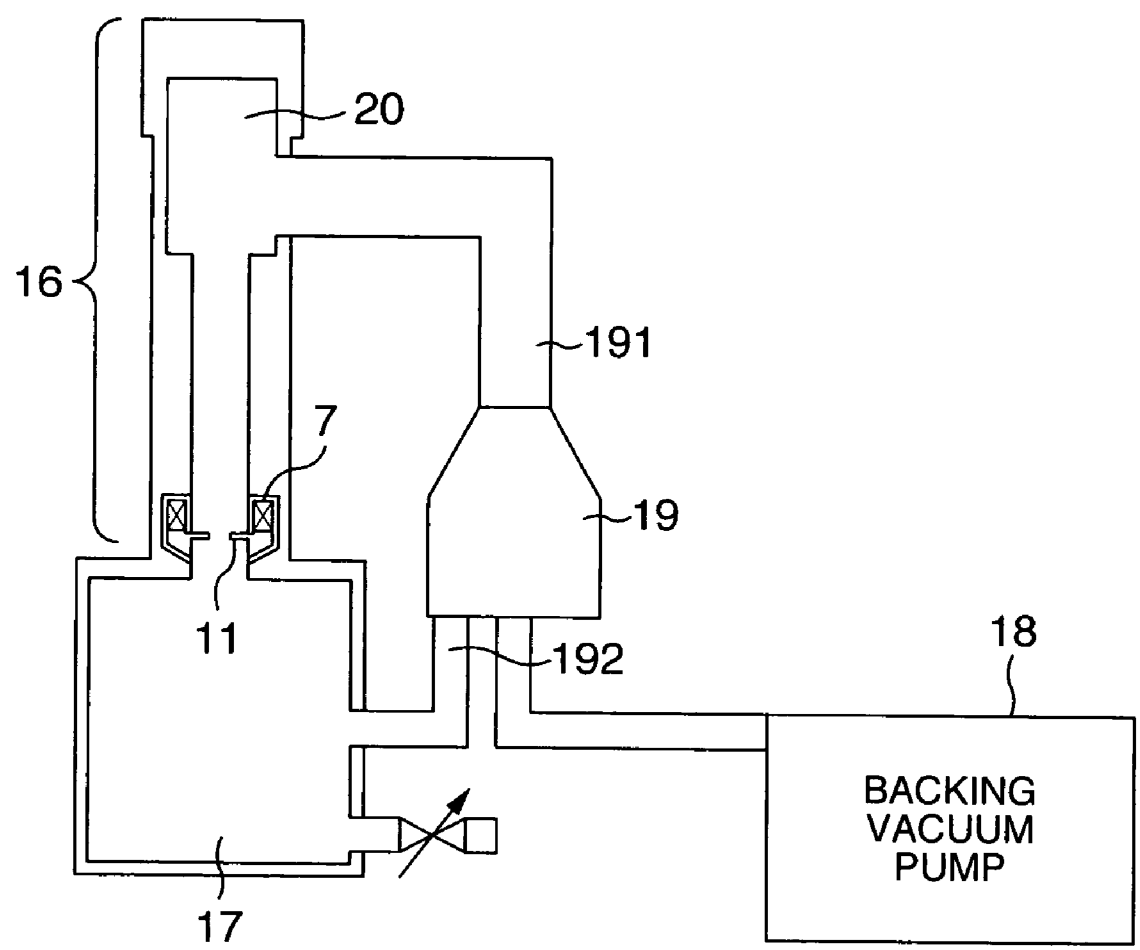
FIG. 6 is a diagram schematically showing another embodiment of the vacuum evacuation system of the environmental scanning electron microscope of the invention.

Referring to FIG. 6, another embodiment of the vacuum evacuation system applicable to the environmental scanning electron microscope of the invention is schematically illustrated therein. Concurrently with start of evacuation, pre-evacuation of main pump 19, electron gun chamber 20 and specimen chamber 17 is effected by means of a backing vacuum pump 18 and after completion of the pre-evacuation, the main pump 19 is started. With the aim of permitting simultaneous evacuation to high vacuum and low vacuum, a composite turbo-molecular pump with main port 191 and intermediate port 192 for low vacuum evacuation is adopted as the main pump 19. Then, with the main port 191 connected to the electron gun chamber 20 for which high vacuum is to be maintained and with the intermediate port 192 connected to the specimen chamber 17 for which low pressure is to be maintained, vacuum evacuation is started. In this manner, one backing vacuum pump can be saved.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An environmental scanning electron microscope comprising three stages of objective apertures used as apertures for an objective lens functioning to focus an electron beam emitted from an electron source and used also as orifices for differential pumping between an electron optical system and a specimen chamber, wherein a deflection fulcrum of the electron beam in the electron optical system is set substantially at a mid stage of said three-stage objective aperture.

2. An environmental scanning electron microscope comprising three stages of objective apertures used as apertures for an objective lens functioning to focus an electron beam emitted from an electron source and used also as orifices for differential pumping between an electron optical system and a specimen chamber, wherein a deflection fulcrum of the electron beam in the electron optical system and a lens principal plane of said objective lens are set substantially at a mid stage of said three-stage objective aperture.

3. An environmental scanning electron microscope according to claim 1, wherein pre-evacuation of main pump, electron gun chamber and specimen chamber is effected by means of a backing vacuum pump and after completion of the pre-evacuation, the specimen chamber is controllably evacuated to low vacuum by the main pump while the electron gun chamber being evacuated to high vacuum thereby.

4. An environmental scanning electron microscope according to claim 3, wherein said backing vacuum pump includes a first backing vacuum pump for pre-evacuation of said main pump and electron gun chamber and a second backing vacuum pump for pre-evacuation of said specimen chamber.

5. An environmental scanning electron microscope according to claim 1, wherein pre-evacuation of main pump and electron gun chamber is effected by means of a backing vacuum pump and after completion of the pre-evacuation, said specimen chamber is evacuated to low vacuum through an intermediate port of said main pump while said electron gun chamber being evacuated to high vacuum through a main port of said main pump.

6. An environmental scanning electron microscope according to claim 2, wherein pre-evacuation of main pump, electron gun chamber and specimen chamber is effected by means of a backing vacuum pump and after completion of the pre-evacuation, the specimen chamber is controllably evacuated to low vacuum by the main pump while the electron gun chamber being evacuated to high vacuum thereby.

7. An environmental scanning electron microscope according to claim 2, wherein pre-evacuation of main pump and electron gun chamber is effected by means of a backing vacuum pump and after completion of the pre-evacuation, said specimen chamber is evacuated to low vacuum through an intermediate port of said main pump while said electron gun chamber being evacuated to high vacuum through a main port of said main pump.

* * * * *